(12) United States Patent
Sakamoto

(10) Patent No.: US 12,246,147 B2
(45) Date of Patent: Mar. 11, 2025

(54) INDWELLING NEEDLE ASSEMBLY

(71) Applicant: NIPRO CORPORATION, Osaka (JP)

(72) Inventor: Shingo Sakamoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 734 days.

(21) Appl. No.: 17/602,455

(22) PCT Filed: Apr. 10, 2020

(86) PCT No.: PCT/JP2020/016151
§ 371 (c)(1),
(2) Date: Oct. 8, 2021

(87) PCT Pub. No.: WO2020/209368
PCT Pub. Date: Oct. 15, 2020

(65) Prior Publication Data
US 2022/0211979 A1  Jul. 7, 2022

(30) Foreign Application Priority Data
Apr. 11, 2019  (JP) ................................. 2019-075905

(51) Int. Cl.
*A61M 25/06*  (2006.01)
(52) U.S. Cl.
CPC .... *A61M 25/0606* (2013.01); *A61M 25/0631* (2013.01); *A61M 25/0693* (2013.01)
(58) Field of Classification Search
CPC .......... A61M 25/0606; A61M 25/0631; A61M 25/0693

(Continued)

(56) References Cited

U.S. PATENT DOCUMENTS

| | | | |
|---|---|---|---|
| 2004/0044313 A1 | 3/2004 | Nakajima | |
| 2015/0080801 A1* | 3/2015 | Tanabe | A61M 25/0631 604/164.01 |

(Continued)

FOREIGN PATENT DOCUMENTS

| | | |
|---|---|---|
| EP | 0753318 B1 | 12/2003 |
| EP | 1861134 B1 | 2/2015 |

(Continued)

OTHER PUBLICATIONS

Extended European Search Report in EP Application No. 20787325.8, issued Apr. 3, 2023, 17 pages.

(Continued)

*Primary Examiner* — Phillip A Gray
(74) *Attorney, Agent, or Firm* — Jason M. Shapiro; Devlin Law Firm LLC

(57) ABSTRACT

An objective of the present invention is to provide an indwelling needle assembly that has a novel structure and improves operability for the practitioner. An indwelling needle assembly 10 in which an inner needle unit 16 comprises a storage housing 14 for storing a protector 52, and which is provided with a connecting member 94 that connects the storage housing 14 to an outer needle hub 20. The protector 52 prevents movement of the connecting member 94 and holds the storage housing 14 and the outer needle hub 20 in a connected state. Deformation or displacement of the protector 52 due to retraction of an inner needle 12 permits the movement of the connecting member 94 and makes it possible to release the connected state between the storage housing 14 and the outer needle hub 20.

5 Claims, 8 Drawing Sheets

(58) Field of Classification Search
USPC .................................................. 604/164.01
See application file for complete search history.

(56) References Cited

U.S. PATENT DOCUMENTS

| | | |
|---|---|---|
| 2015/0202412 A1 | 7/2015 | Nakajima et al. |
| 2017/0035995 A1 | 2/2017 | Shevgoor et al. |
| 2018/0043093 A1* | 2/2018 | Nakagami ......... A61M 25/0693 |

FOREIGN PATENT DOCUMENTS

| | | |
|---|---|---|
| EP | 3238770 A1 | 11/2017 |
| JP | 2004-24622 A | 1/2004 |
| JP | 2018-23587 A | 2/2018 |
| JP | 2018/023587 A | 2/2018 |
| JP | 2018/117807 A | 8/2018 |
| WO | 2013/027355 A1 | 2/2013 |
| WO | 2013/171851 A1 | 11/2013 |
| WO | 2016/080525 A1 | 5/2016 |

OTHER PUBLICATIONS

Partial European Search Report in EP Application No. 20787325.8, issued Jan. 3, 2023, 19 pages.
International Search Report issued in International Patent Application No. PCT/JP2020/016151 mailed Jun. 30, 2020 (4 pages), with English translation.
Office Action for corresponding JP Application No. 2021-513718, issued Oct. 26, 2023, including English translation, 14 pages.
English Translation of International Preliminary Report on Patentability for International Application No. PCT/JP2020/016151 issued on Sep. 28, 2021 (6 pages).
Office Action from corresponding Japanese Patent Application No. 2024-017069, issued Jun. 19, 2024, with English translation (7 pages).

* cited by examiner

INDWELLING NEEDLE ASSEMBLY

CROSS REFERENCE TO RELATED APPLICATIONS

This application is a U.S. National Stage of International Application No. PCT/JP2020/016151, filed on Apr. 10, 2020, and claims priority under 35 U.S.C. § 119 to Japanese Application No. JP 2019-075905, filed on Apr. 11, 2019, the contents of which are incorporated by reference herein in their entirety.

TECHNICAL FIELD

The present invention relates to an indwelling needle assembly adapted to be used for puncture when performing infusion, blood collection, hemodialysis, or the like.

BACKGROUND ART

Conventionally, an indwelling needle assembly including an inner needle unit and an outer needle unit has been known as a medical tool for performing treatments such as infusion, blood collection, and hemodialysis. In such an indwelling needle assembly, a protector that protects the retracted inner needle may be adopted in order to prevent inadvertent puncture by the inner needle retracted after puncturing. An indwelling needle assembly provided with a protector is disclosed in, for example, Japanese Unexamined Patent Publication No. JP-A-2004-24622 (Patent Document 1).

Such an indwelling needle assembly is operated in such a way that, after puncturing with the outer needle penetrated by the inner needle, the inner needle is retracted and the inner needle unit is detached while the outer needle unit is indwelled in the patient.

BACKGROUND ART DOCUMENT

Patent Document

Patent Document 1: JP-A-2004-24622

SUMMARY OF THE INVENTION

Problem the Invention Attempts to Solve

However, in the indwelling needle assembly of the conventional structure, there is room for improvement in the operability of the practitioner. For example, when the inner needle unit is detached after puncture, the outer needle unit may be pulled by the inner needle unit and come off from the puncture target site, and there is room for improvement. For example, in the indwelling needle assembly described in Patent Document 1, since the tip of the second telescopic pipe 21 is in a state of being tightly fitted into the engagement hole 11B of the hemostatic adapter 11, the outer needle may be pulled by the inner needle and come off from the puncture target site. The practitioner has to fix the outer needle unit with one hand while retracting the inner needle unit with the other hand, which requires a special operation.

It is an object of the present invention to provide an indwelling needle assembly with a novel structure which is able to improve the operability of a practitioner.

Means for Solving the Problem

Hereinafter, preferred embodiments for grasping the present invention will be described. However, each preferred embodiment described below is exemplary and can be appropriately combined with each other. Besides, a plurality of elements described in each preferred embodiment can be recognized and adopted as independently as possible, or can also be appropriately combined with any element described in other preferred embodiments. By so doing, in the present invention, various other preferred embodiments can be realized without being limited to those described below.

A first preferred embodiment provides an indwelling needle assembly comprising: an inner needle unit including an inner needle hub; an outer needle unit including an outer needle hub, the inner needle unit and the outer needle unit being detachably connected to each other; and an inner needle to which a protector is attached, the inner needle being retractably inserted through an outer needle, while the protector being configured to deform or displace to protect a needle tip of the inner needle by being moved to the needle tip due to retraction of the inner needle, wherein a storage housing storing the protector is provided to the inner needle unit, a connecting member connecting the storage housing to the outer needle hub is provided, the protector prevents the connecting member from moving such that the storage housing and the outer needle hub are held in a connected state, and the connecting member is configured to be permitted to move by the protector deforming or displacing due to the retraction of the inner needle such that the connected state of the storage housing and the outer needle hub is allowed to be released.

According to the indwelling needle assembly structured following the present preferred embodiment, by skillfully utilizing the protector that elastically deforms due to the retraction of the inner needle, the connected state by the connecting member connecting the storage housing and the outer needle hub is allowed to be released. It is not necessary to move the entire outer needle unit in the axis-perpendicular direction with respect to the inner needle unit, and the work can be facilitated.

As the protector in the present preferred embodiment, it is also possible to adopt, for example, an elastically deformable protector configured to be prevented from elastic deformation by an inserted inner needle to hold the connecting member in a connected state between the storage housing and the outer needle hub, and to elastically deform due to the retraction of the inner needle thereby allowing the connecting member to move.

A second preferred embodiment provides the indwelling needle assembly according to the first preferred embodiment, wherein the connecting member includes a locking part locked to a proximal end opening part of the outer needle hub, a distal end portion of the storage housing is inserted from the proximal end opening part of the outer needle hub, and a peripheral wall of the outer needle hub is sandwiched by the locking part of the connecting member and the distal end portion of the storage housing from an inside and an outside.

According to the indwelling needle assembly structured following the present preferred embodiment, the connection between the outer needle unit and the inner needle unit before the retraction of the inner needle can be realized more stably.

A third preferred embodiment provides the indwelling needle assembly according to the first or second preferred embodiment, wherein the connecting member includes a through hole communicating with an inner hole of the storage housing, and the protector, the protector being prevented from elastic deformation by the inner needle being inserted through the protector, is in contact with both inner surfaces of the inner hole and the through hole such that the connecting member is prevented from moving with respect to the storage housing.

According to the indwelling needle assembly structured following the present preferred embodiment, the stability of positioning of the connecting member with respect to the storage housing by the protector can be improved before the retraction of the inner needle, thereby minimizing rattling of the connecting member, for example.

A fourth preferred embodiment provides the indwelling needle assembly according to any of the first through third preferred embodiments, wherein contact portions between an inner surface of the storage housing and the protector, the protector being prevented from elastic deformation by the inner needle being inserted through the protector, are in planar contact with each other.

According to the indwelling needle assembly structured following the present preferred embodiment, the stability of the position of the protector with respect to the storage housing can be improved by setting the contact area of the protector with respect to the storage housing in the circumferential direction. As a result, the position stability of the connecting member whose movement is restricted by the protector with respect to the storage housing can also be improved.

A fifth preferred embodiment provides the indwelling needle assembly according to any of the first through fourth preferred embodiments, wherein the storage housing includes a pair of grasping parts provided on an outer circumferential surface of the storage housing in a portion located on a distal end side.

According to the indwelling needle assembly structured following the present preferred embodiment, the practitioner can grasp the part near the needle tip end, and the puncture operation is stably realized.

A sixth preferred embodiment provides the indwelling needle assembly according to any of the first through fifth preferred embodiments, wherein an inclined surface is provided in a portion where the connecting member and the outer needle hub are locked, and the connecting member is configured to move along the inclined surface due to the retraction of the inner needle such that connection between the connecting member and the outer needle hub is released.

According to the indwelling needle assembly structured following the present preferred embodiment, it is not necessary to provide a special urging means to displace the connecting member, and the lock of the connecting member with the outer needle hub can be released only by retracting the inner needle.

Besides, in the indwelling needle assembly according to any one of the first to sixth preferred embodiments, it would also be possible to adopt a preferred embodiment in which, by retracting the inner needle, the connecting member is allowed to move toward a lateral side with respect to the storage housing, which is the direction along the body surface of the patient.

According to the indwelling needle assembly structured following the present preferred embodiment, the movement of the connecting member during detachment of the inner needle unit can be performed toward the lateral side, avoiding movement to the lower part where the body surface of the patient is located and the upper part where the practitioner operates. Therefore, it is possible to prevent the practitioner from interfering with the connecting member during operation to cause deterioration in operability.

A seventh preferred embodiment provides an indwelling needle assembly comprising: an inner needle unit including an inner needle hub; an outer needle unit including an outer needle hub, the inner needle unit and the outer needle unit being detachably connected to each other; an inner needle retractably inserted through an outer needle; a storage housing configured to store the inner needle due to retraction of the inner needle; a connecting member connecting the storage housing to the outer needle unit; and a preventing member provided between the inner needle and the connecting member, the preventing member preventing the connecting member from moving such that the storage housing and the outer needle unit are maintained in a connected state by the connecting member, the connecting member being configured to be permitted to move by the preventing member displacing due to the retraction of the inner needle such that the connected state of the storage housing and the outer needle unit is allowed to be released.

According to the indwelling needle assembly structured following the present preferred embodiment, the preventing member for preventing the movement of the connecting member connecting the storage housing and the outer needle unit is provided, and due to the retraction of the inner needle, the preventing member displaces, thereby allowing the connected state of the storage housing and the outer needle unit by the connecting member to be released. Therefore, for example, it is possible to compatibly improve the stability of the connected state of the storage housing and the outer needle unit and the operability of releasing the connected state.

Further, in the indwelling needle assembly provided with the protector, the following eighth preferred embodiment may also be adopted.

An eighth preferred embodiment provides an indwelling needle assembly comprising: an inner needle that is retractable; a protection housing configured to store the inner needle after retraction of the inner needle; and a displacing member stored in a distal end portion of the protection housing and configured to displace due to the retraction of the inner needle, wherein the protection housing has a multi-cylinder structure comprising a plurality of tubular bodies, and the tubular bodies are disposed within one another at a position away to a proximal end side of the protection housing from an attachment position of the displacing member, and the tubular bodies are configured to be sequentially pulled out by the inner needle being retracted such that the inner needle is stored in the protection housing.

According to the indwelling needle assembly structured following the present preferred embodiment, the protection housing has a structure in which the plurality of tubular bodies are disposed within one another, so that the protection housing, and hence the indwelling needle assembly can be downsized in the length direction. In particular, the tubular bodies are disposed within one another on the proximal end side with respect to the attachment position of the protector. Thus, in comparison with the case where, for example, the tubular bodies are disposed within one another on the radially outer side of the protector, it is possible to achieve downsizing in the radial direction as well.

Further, in the indwelling needle assembly according to the present preferred embodiment, the presence of the displacing member makes it possible for the displacing member to have the function of the protection housing in the indwelling needle assembly including the protection housing, thereby improving the operational stability. For example, by using the displacing member as a protector that covers the needle tip, it is possible to more effectively prevent the exposure of the inner needle tip end. For example, by preventing the displacing member from being separated from the protection housing, the displacing member can prevent the protection housing from returning to the initial state from the state in which the inner needle is stored. Thus, it is not necessary to provide a locking mechanism to the tubular body itself constituting the protection housing, thereby preventing the situation in which, due to the resistance when the tubular bodies are locked to each other, the inner needle unit is separated from the outer needle unit. For example, by using the displacing member as a member that prevents the connecting member from moving, the retraction operation of the inner needle can be performed in conjunction with the disconnection of the connecting member. By dividing the functions in this way, it is possible to maintain the small size while enhancing the operational stability, thereby improving the operability of the practitioner as well.

In addition, in the indwelling needle assembly according to the present preferred embodiment, it is also possible to concomitantly implement the indwelling needle assembly according to any of the preceding first through seventh preferred embodiments. At that time, it is also possible to constitute the storage housing for storing the protector in the indwelling needle assembly according to any of the preceding first through seventh preferred embodiments by using the protection housing according to the present preferred embodiment.

Moreover, in the indwelling needle assembly, the following ninth preferred embodiment may also be adopted.

A ninth preferred embodiment provides an indwelling needle assembly comprising: an inner needle; and an outer needle through which the inner needle is retractably inserted, wherein a protection housing configured to store the inner needle after retraction of the inner needle is provided, and the protection housing has a multi-cylinder structure in which a plurality of tubular bodies are disposed within one another, and the tubular bodies are configured to be sequentially pulled out by the inner needle being retracted, and a proximal end of the tubular body, the tubular body being configured to be on a most proximal end side among the tubular bodies after being sequentially pulled out, includes a proximal end wall having a penetration hole penetrating through the proximal end wall.

According to the indwelling needle assembly structured following the present preferred embodiment, the storage housing has a structure in which the plurality of tubular bodies are disposed within one another, so that the storage housing, and hence the indwelling needle assembly can be downsized in the length direction. In such a storage housing, by providing a penetration hole that penetrates the housing, the negative pressure inside the housing can be reduced even during a quick retracting operation or the like, and the tubular body can be pulled out more quickly as well. In addition, in the indwelling needle assembly according to the present preferred embodiment, it is also possible to concomitantly implement the indwelling needle assembly according to any of the preceding first through eighth preferred embodiments. At that time, it is also possible to constitute the storage housing for storing the protector in the indwelling needle assembly according to any of the preceding first through seventh preferred embodiments or the protection housing in the indwelling needle assembly according to the eighth preferred embodiment by using the protection housing according to the present preferred embodiment.

Effect of the Invention

According to the present invention, it is possible to provide an indwelling needle assembly having a novel structure capable of solving at least one of the problems inherent in the indwelling needle assembly of the conventional structure, namely, the novel structure in which the inner needle unit can be easily detached from the outer needle unit and the operability of the practitioner can be improved or the like.

EMBODIMENTS FOR CARRYING OUT THE INVENTION

Figure 1:
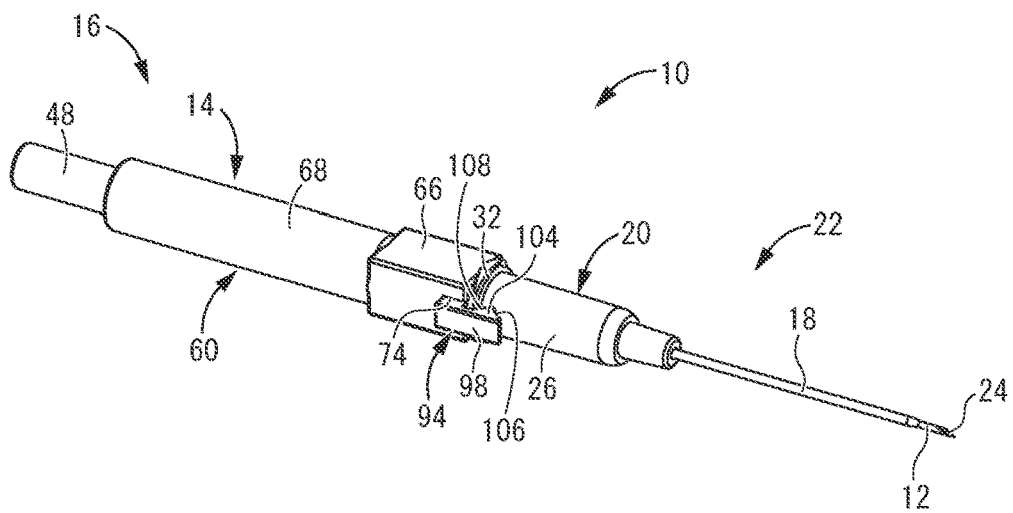
FIG. 1 is a perspective view showing an indwelling needle assembly according to a first practical embodiment of the present invention.
Figure 2:
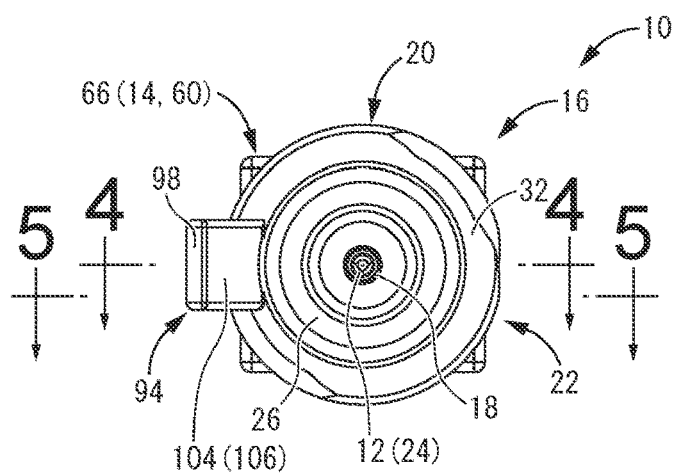
FIG. 2 is an enlarged front view of the indwelling needle assembly shown in FIG. 1.
Figure 3:
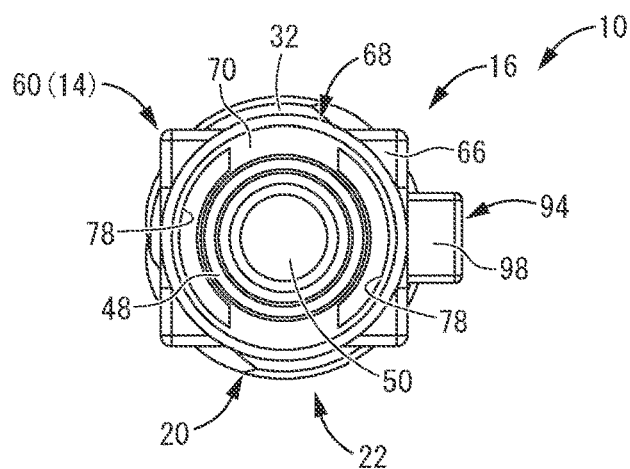
FIG. 3 is an enlarged rear view of the indwelling needle assembly shown in FIG. 1.

In order to clarify the present invention more specifically, practical embodiments of the present invention will be described in detail below in reference to the drawings.

First, FIGS. 1 to 7 show an indwelling needle assembly 10 according to a first practical embodiment of the present invention. The indwelling needle assembly 10 includes an inner needle unit 16 including an inner needle 12 and an inner needle hub 14, and an outer needle unit 22 including an outer needle 18 and an outer needle hub 20. In the state before use shown in FIGS. 1 to 7, the inner needle 12 is retractably inserted through the outer needle unit 22 from the proximal end side, and the inner needle unit 16 and the outer needle unit 22 are connected to each other. In the following description, the axial direction means the left-right direction in FIG. 4, which coincides with the needle axis direction of the inner needle 12 and the outer needle 18. Besides, the distal end side means the left side in FIG. 4 which coincides with a needle tip 24 side of the inner needle 12, while the proximal end side means the right side in FIG. 4 which coincides with the side which the user grips and operates.

More specifically, the outer needle 18 has a tube shape having a shorter length than that of the inner needle 12, and has flexibility. The outer peripheral surface of the distal end portion of the outer needle 18 may be, for example, a tapered surface whose diameter gradually decreases toward the distal end side, whereby the puncture resistance to the living body can be reduced. Further, one or a plurality of penetration holes may be provided in the peripheral wall at the distal end portion of the outer needle 18, whereby the flow efficiency of the fluid with respect to the outer needle 18 can be improved.

The outer needle hub 20 has a generally tubular shape extending in the axial direction overall, and in the present practical embodiment, the outer needle hub 20 includes a peripheral wall 26 of generally cylindrical shape. On the inner circumferential surface of the distal end portion of the peripheral wall 26, a caulking pin 28 of generally cylindrical shape is fastened. By the proximal end portion of the outer needle 18 being sandwiched between the peripheral wall 26 and the caulking pin 28 and being bonded or welded as needed, the outer needle hub 20 is fixed to the proximal end side of the outer needle 18.

A proximal end opening part 30 of the outer needle hub 20 is provided with a flanged part 32 projecting radially outward over generally the entire circumference in the circumferential direction, and a screw thread is provided on the outer circumferential surface of the flanged part 32. With this configuration, a luer-lock type syringe, connector, or the like can be connected to the outer needle hub 20. In the present practical embodiment, a positioning groove 34 extending in the axial direction is provided in a part of the circumference of the flanged part 32 (upper side in FIG. 4).

In the present practical embodiment, a hemostasis valve mechanism 36 is incorporated in the outer needle hub 20 in a stored state. The hemostasis valve mechanism 36 includes a disc valve 38, a pusher 40, and a pusher guide 42. When the inner needle 12 is retracted, the blood flowing back through the outer needle 18 is stored in the region on the distal end side with respect to the hemostasis valve mechanism 36 of the outer needle hub 20. Thus, by making at least the distal end side with respect to the arrangement position of the hemostasis valve mechanism 36 transparent, the flashback can be confirmed from the outside.

The disc valve 38 is formed of an elastic body such as rubber or an elastomer, and a slit 44 is formed in the center thereof. The pusher 40 of generally tubular shape is located on the proximal end side of the disc valve 38, and the pusher guide 42 of generally tubular shape is mated in a concave and convex manner between the pusher 40 and the peripheral wall 26 of the outer needle hub 20 on the radially outer side of the pusher 40, so that the pusher guide 42 is positioned with respect to the peripheral wall 26.

By connecting a syringe or the like to the outer needle hub 20 provided with such a hemostasis valve mechanism 36, the pusher 40 pushed toward the distal end side by a male luer such as a syringe is moved to the distal end side by the guiding action of the pusher guide 42, so that the slit 44 of the disc valve 38 can be pushed open. Further, by removing the syringe or the like from the outer needle hub 20, the disc valve 38 elastically undergoes recovering deformation, so that the slit 44 of the disc valve 38 can be closed.

The inner needle 12 is formed of a known material such as stainless steel, aluminum, titanium, or an alloy thereof, and is a hollow needle in the present practical embodiment. The inner needle 12 may be a solid needle. The distal end of the inner needle 12 comprises a sharp needle tip 24. Meanwhile, the proximal end of the inner needle 12 is inserted or press-fitted into a fixing tube part 46 provided to the inner needle hub 14, and is bonded or welded as needed, so that the inner needle hub 14 is fixed to the proximal end side of the inner needle 12.

The inner needle hub 14 has a generally tubular shape extending in the axial direction overall, and in the present practical embodiment, the aforementioned fixing tube part 46 is provided at the proximal end of the inner needle hub 14. In the inner needle hub 14, the formation position of the fixing tube part 46 has a double-cylinder structure, and a storing tube part 48 is provided on the radially outer side of the fixing tube part 46. It is preferable that at least the storing tube part 48 of the inner needle hub 14 is transparent, and the blood flowing back through the inner needle 12 when the indwelling needle assembly 10 is stuck is stored in the storing tube part 48, so that the flashback can be confirmed from the outside. A ventilation filter 50 is provided at the proximal end opening part of the storing tube part 48, and when the blood is stored, the air in the storing tube part 48 is discharged through the ventilation filter 50, while blood leakage from the storing tube part 48 is prevented by the ventilation filter 50.

Besides, the inner needle unit 16 includes a protector 52 serving as a preventing member and serving as a displacing member, which protects the needle tip 24 of the inner needle 12 after use. The protector 52 is externally attached onto the inner needle 12 so as to be movable in the axial direction. Whereas the structure of the protector is not limited, the protector 52 of the present embodiment is formed by pressing a blank metal plate or the like, and is made elastically deformable by adopting spring steel or the like.

Figure 4:
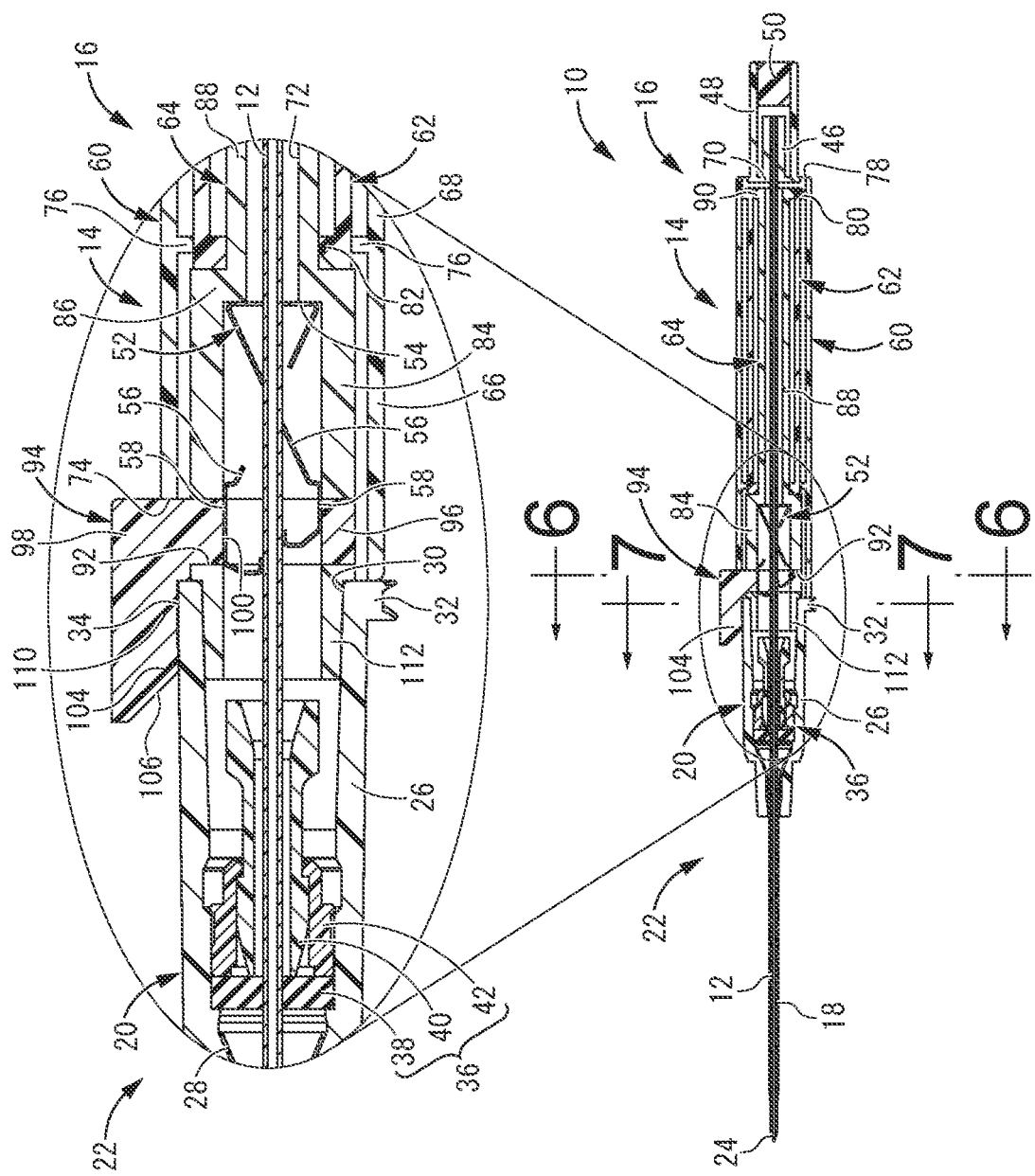
FIG. 4 is a cross sectional view taken along line 4-4 of FIG. 2.
Figure 5:
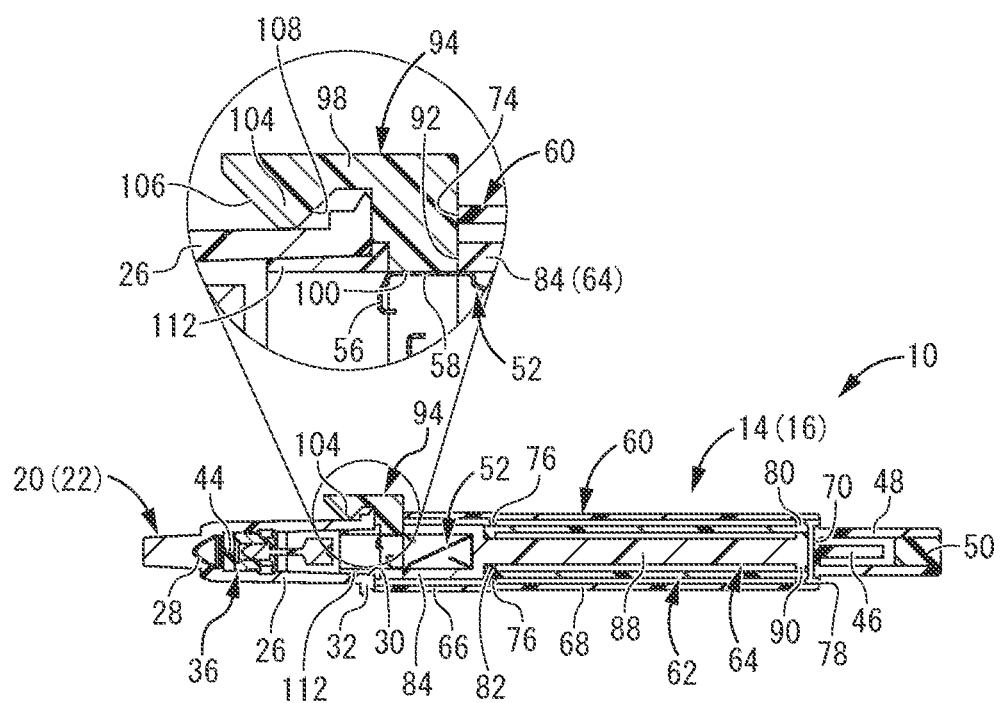
FIG. 5 is a cross sectional view taken along line 5-5 of FIG. 2.
Figure 6:
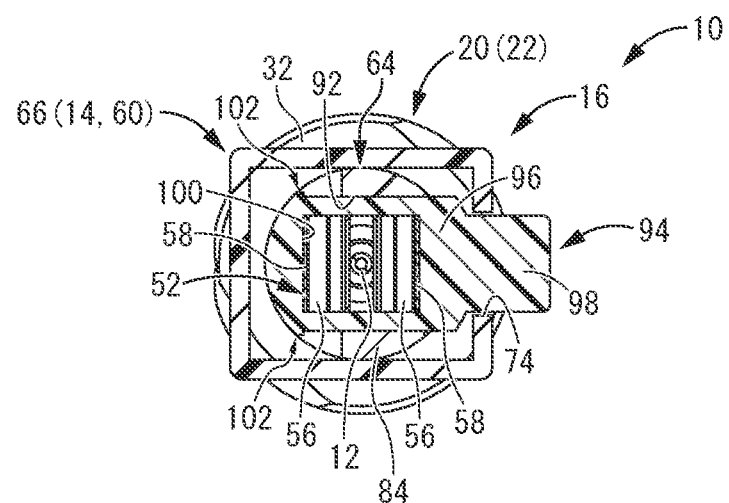
FIG. 6 is an enlarged transverse cross sectional view taken along line 6-6 of FIG. 4.
Figure 7:
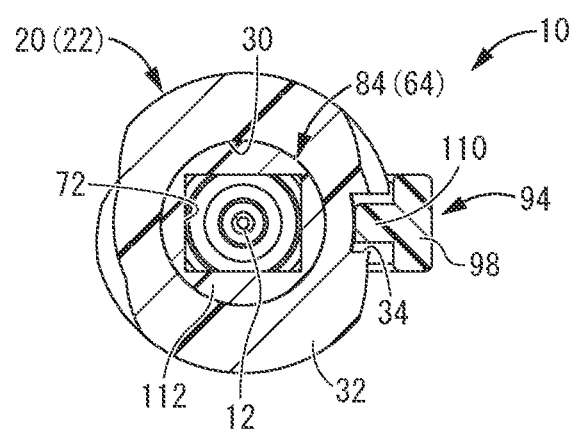
FIG. 7 is an enlarged transverse cross sectional view taken along line 7-7 of FIG. 4.
Figure 8:
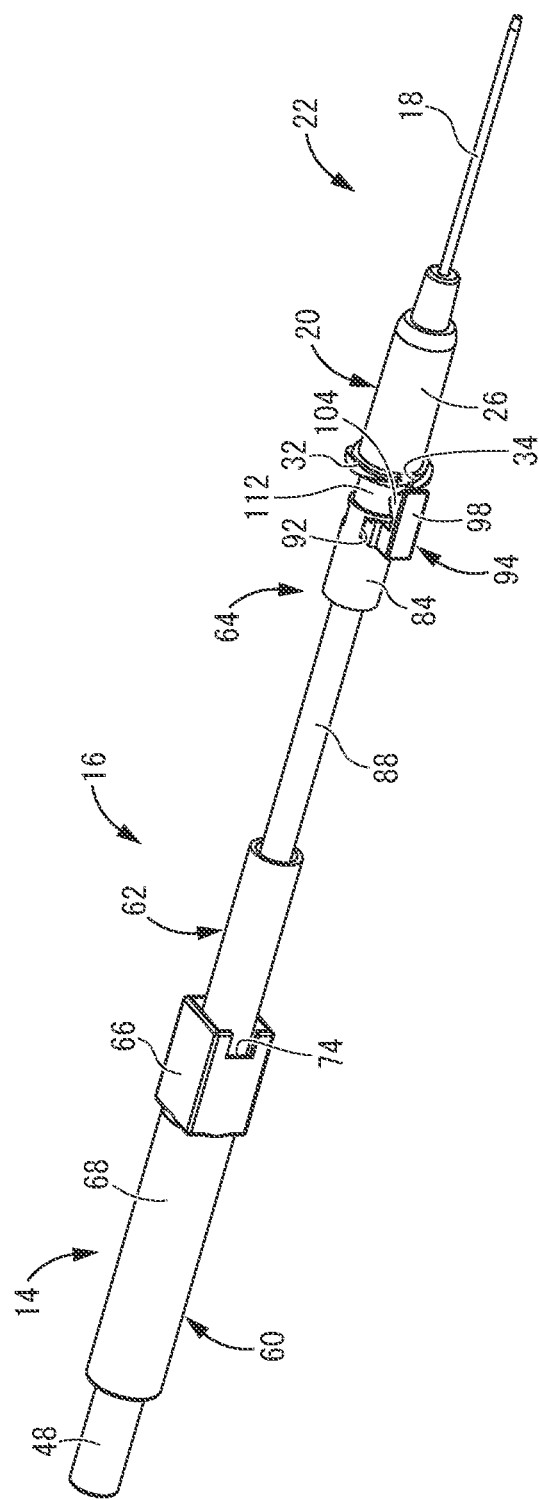
FIG. 8 is perspective view of the indwelling needle assembly of FIG. 1, showing a state in which an inner needle unit is detached from an outer needle unit.

That is, the protector 52 includes a rear wall 54 and a pair of elastic arm parts 56, 56 protruding toward the distal end side from the opposite sides of the rear wall 54 (the vertically opposite sides in FIG. 4). These elastic arm parts 56, 56 intersect with each other and extend to the distal end side, and are elastically deformable in a direction in which the distal end portions approach or separate from each other. The elastic arm parts 56, 56 have different axial dimensions from each other, and when the inner needle 12 is retracted, the distal end portions of the elastic arm parts 56, 56 displace in the direction of approaching each other so as to overlap each other in the axial direction.

By inserting the inner needle 12 through such a protector 52, the distal end portions of the elastic arm parts 56, 56 are pushed apart in a direction in which they are separated from each other. That is, the distal end portions of the elastic arm parts 56, 56 are subjected to urging force in the direction of approaching each other based on the elastic recovering deformation. By coming into contact with the inner needle 12, the distal end portions of the elastic arm parts 56, 56 are prevented from deformation in the direction of approaching each other.

In the present practical embodiment, the distal end portions of the elastic arm parts 56, 56 through which the inner needle 12 is inserted and pushed apart are provided with a region extending parallel to the axial direction. In particular, in the present practical embodiment, the protector 52 is formed with a certain widthwise dimension (the vertical dimension in FIG. 6). Thus, the distal end portions of the elastic arm parts 56, 56 are provided with respective flat plate parts 58, 58 having a generally rectangular shape.

Here, the inner needle unit 16 includes a generally tubular storage housing in which the aforementioned protector 52 is stored, and in the present practical embodiment, the storage housing is constituted by the inner needle hub 14. In particular, in the present practical embodiment, the inner needle hub 14 has a multi-cylinder structure in which a plurality of (three) tubular bodies extending in the axial direction are disposed within one another in a generally concentric manner, and comprises a first tubular body 60 located on a radially outermost side, a second tubular body 62 located on a radially middle part, and a third tubular body 64 located on a radially innermost side. These first to third tubular bodies 60, 62, 64 are combined with a telescopic structure in which they are disposed within one another so as to be extendable and contractible in the axial direction. As will be described below, in the present practical embodiment, the inner needle hub in a narrow sense in which the proximal end side of the inner needle 12 is fixed is the first tubular body 60. However, since the tubular bodies are integrally combined in a connected state, the inner needle hub in a broad sense is constituted by the first to third tubular bodies 60, 62, 64 in cooperation with each other. Further, in a narrow sense, a large diameter tube part 84 (described later) on the distal end side of the third tubular body 64 constitutes the storage housing 14 of the protector 52, and the first to third tubular bodies 60, 62, 64 constitute a protection housing for storing the inner needle 12 after retraction.

That is, the shape and diameter dimension of the first tubular body 60 are varied in the axial direction, namely, the distal end portion comprises a rectangular tube part 66 having a rectangular cross section, while the axially middle portion comprises a cylinder part 68 having a circular cross section. By providing the rectangular tube part 66 on the first tubular body 60 located on the radially outermost side, the user can grasp the rectangular tube part 66 by placing the fingertips of the hand on the outer peripheral surface thereof in a stably touching manner (for example, the user grasps the rectangular tube part 66 so as to sandwich it between the thumb and the middle finger from the opposite sides). This facilitates the retraction operation of the inner needle 12 and the delivery operation of the outer needle hub 20 to the distal end side with the fingertip of the forefinger described later.

In particular, as shown in FIGS. 1 and 4, in the initial state in which the inner needle unit 16 and the outer needle unit 22 are connected and the needle tip 24 of the inner needle 12 projects from the outer needle 18 so that the puncture is possible, in the portion located on the distal end side of the inner needle unit 16, the distal end portions of the first tubular body 60 and the third tubular body 64 is arranged so as to be continuous with the proximal end side of the outer needle hub 20. Then, the rectangular tube part 66 of the first tubular body 60 is externally placed about the large diameter tube part 84 to be described later that is provided at the distal end of the third tubular body 64 and stores the protector 52, and the rectangular tube part 66 covers the outer circumferential surface of the large diameter tube part 84.

It is desirable that the first tubular body 60 and the third tubular body 64 include parts at a plurality of places on the circumference that are in contact with or close to each other directly or indirectly via another member in the axis-perpendicular direction so as to suppress rattling in the axis-perpendicular direction. Further, the outer peripheral surface of the rectangular tube part 66 of the first tubular body 60 has a generally rectangular cross section. For example, the practitioner sandwiches such a grasping part with fingertips from the opposite sides and touches the grasping part with another fingertip from above. This makes it easy for the practitioner to attach fingertips to each of the three surfaces of the rectangular tube part 66 excluding the surface located on the body surface side of the patient for stable grasping. The shape of the outer surface is not particularly limited, but in order to further facilitate the gripping operation with the fingertips, it is preferable that a pair of grasping parts are formed on the outer peripheral surface, for example, on the opposite side surfaces or the like. For ease of grasping, it would also be possible for the grasping part, for example, to be a concave curved surface, to be provided with a non-slip surface due to fine irregularities or the like, or to be provided with a shape or a mark to indicate that it is a grasping part. Moreover, in consideration of catching of fingers on the connecting member 94 to be described later or the like, it would also be possible to appropriately change designs of the shape or position of the outer peripheral surface of the rectangular tube part 66 or the projecting distal end face of the connecting member 94 thereby suppressing the projection of the connecting member 94 from the outer peripheral surface of the rectangular tube part 66, to provide a wall on the connecting member 94 or the peripheral zone of the grasping part, or to appropriately change designs of the shape or position of the grasping part thereby preventing the fingers from being caught on the connecting member 94.

Besides, the aforementioned storing tube part 48 and fixing tube part 46 are integrally formed at the proximal end portion of the first tubular body 60. The outer diameter dimension of the storing tube part 48 is smaller than the outer diameter dimension of the cylinder part 68, that is, a proximal end wall 70 is provided at the proximal end of the cylinder part 68, and the storing tube part 48 having a diameter smaller than that of the cylinder part 68 projects from the proximal end wall 70 toward the proximal end side. Additionally, the inner needle 12 fixed to the fixing tube part 46 extends toward the distal end side through an inner hole 72 of the third tubular body 64.

At the distal end of the rectangular tube part 66, a generally rectangular notch 74 into which the connecting member 94 described later is fitted is formed in a part in the circumferential direction (in the upper part in FIG. 4). Further, a first engaging claw 76 projecting radially inward is provided on the inner circumferential surface of the rectangular tube part 66 or the cylinder part 68. In the present practical embodiment, the pair of first engaging claws 76, 76 extend in the circumferential direction with a circumferential dimension of half a circumference or less, and are formed so as to be opposed to each other on the opposite sides in the vertical direction in FIG. 4. In particular, in the present practical embodiment, in the proximal end wall 70, a pair of penetration holes 78, 78 penetrating through the proximal end wall 70 are formed at positions corresponding to the pair of first engaging claws 76, 76. With this configuration, when the first tubular body 60 is formed by injection molding, the penetration hole 78 can also be used as a hole for demolding in order to form the first engaging claw 76.

The second tubular body 62 has a generally constant diameter dimension across the entire length in the axial direction, and has an axial dimension shorter than that of the first tubular body 60. In the present practical embodiment, the second tubular body 62 has an axial dimension generally equal to that of the cylinder part 68 of the first tubular body 60. A second proximal end engaging claw 80 projecting radially outward is provided at the proximal end of the second tubular body 62, and a second distal end engaging claw 82 projecting radially inward is provided at the distal end of the second tubular body 62. In the present practical embodiment, these second proximal end engaging claw 80 and second distal end engaging claw 82 are formed in an annular shape over the entire circumference in the circumferential direction.

The third tubular body 64 has a generally stepped cylindrical shape whose diameter dimension is varied in the axial direction overall. That is, the distal end portion of the third tubular body 64 comprises a large diameter tube part 84 having a certain axial dimension and constituting the storage housing of the protector 52. Besides, on the proximal end side with respect to the large diameter tube part 84, a small diameter tube part 88 is formed via an annular wall 86 extending in the axis-perpendicular direction. With this configuration, the inner diameter dimension of the inner hole 72 in the third tubular body 64 is also varied in the axial direction, and the inner diameter dimension of the large diameter tube part 84 is larger than the inner diameter dimension of the small diameter tube part 88. In the present practical embodiment, the inner circumferential shape of the large diameter tube part 84 is generally rectangular, and the inner circumferential shape of the small diameter tube part 88 is circular.

The outer diameter dimension of the large diameter tube part 84 is larger than the outer diameter dimension of the second tubular body 62, and is smaller than the inner diameter dimension of the first tubular body 60. Further, the outer diameter dimension of the small diameter tube part 88 is smaller than the inner diameter dimension of the second tubular body 62. With this configuration, in the formation position of the small diameter tube part 88, the first, second, and third tubular bodies 60, 62, 64 are disposed within one another, and the large diameter tube part 84 is stored in the radial inside of the rectangular tube part 66 of the first tubular body 60 on the distal end side with respect to of the second tubular body 62.

The axial dimension of the small diameter tube part 88 is generally equal to the axial dimension of the second tubular body 62, and the axial dimension of the large diameter tube part 84 is larger than the axial dimension of the rectangular tube part 66 of the first tubular body 60. With this configuration, in a state where the first, second, and third tubular bodies 60, 62, 64 are disposed within one another, the distal end of the third tubular body 64 projects to the distal end side with respect to the distal end of the first tubular body 60.

Besides, a third engaging claw 90 projecting radially outward is provided at the proximal end of the small diameter tube part 88. In the present practical embodiment, the third engaging claw 90 is formed in an annular shape over the entire circumference in the circumferential direction.

The protector 52 is inserted from the distal end side into the radial inside of the large diameter tube part 84, in which the inner diameter dimension of the inner hole 72 of the third tubular body 64 is increased, and is stored therein. In the present practical embodiment, the protector 52 is inserted all the way to the innermost part of the large diameter tube part 84. That is, the rear wall 54 of the protector 52 and the annular wall 86 of the third tubular body 64 are in contact with each other, and the protector 52 is fixed to the third tubular body 64 by a conventionally known fixing means such as a concave and convex mating, a locking structure, or the like. However, the rear wall 54 and the annular wall 86 do not need to be in contact with each other, and with the two walls 54, 86 being remote from each other, the protector 52 may be fixed to the third tubular body 64. In particular, in the present practical embodiment, by the protector 52 being stored in the large diameter tube part 84, the inner surface of the large diameter tube part 84 and the flat plate parts 58, 58 of the protector 52 are in contact with each other.

Here, a passage hole 92 penetrating in the vertical direction in FIG. 4 is formed in the axially middle portion of the large diameter tube part 84 of the third tubular body 64. The passage hole 92 is formed as a rectangular hole having a certain axial dimension and a certain widthwise dimension (the vertical dimension in FIG. 6).

A connecting member 94 that connects the inner needle unit 16 and the outer needle unit 22 is fitted into and attached to the passage hole 92. The connecting member 94 is constituted as a separate body from the protection housing, and includes a passage part 96 fitted into the passage hole 92, and a connecting part 98 that connects the inner needle unit 16 and the outer needle unit 22 outside the indwelling needle assembly 10. The connecting part 98 is continuously provided with respect to one end of the passage part 96 (the upper end in FIG. 4). Since the connecting member 94 is fitted into fitted into and attached to the passage hole 92, it is also possible to understand the connecting member 94 as a part of the inner needle unit 16.

The passage part 96 has a generally rectangular plate shape, and has an axial dimension and a widthwise dimension that are generally equal to those of the passage hole 92. A through hole 100 of generally rectangular shape penetrating in the plate thickness direction (the axial direction) is formed in a generally central portion of the passage part 96. The inner circumferential shape of the through hole 100 is a generally rectangular shape corresponding to the inner circumferential shape of the large diameter tube part 84. In a state where the connecting member 94 is fitted into the passage hole 92 (the state before use), the inner hole of the large diameter tube part 84 and the through hole 100 communicate with each other. At the end of the passage part 96 on the side opposite to the side where the connecting part 98 is provided, retaining projections 102, 102 projecting to the outer side in the width direction with respect to the opening peripheral edge of the passage hole 92 are provided on the both sides in the width direction.

Further, the connecting part 98 has a width dimension smaller than that of the passage part 96, and protrudes to the outside through the notch 74 of the first tubular body 60, while extending up to the distal end side with respect to the rectangular tube part 66. At the distal end of the connecting part 98, a locking part 104 projecting radially inward is provided. The locking part 104 has a claw shape having a generally triangular cross section, and a distal side end face 106 and a proximal side end face 108 of the locking part 104 comprise inclined surfaces that are inclined radially inward in a direction of getting closer to each other. In the present practical embodiment, on the inner circumferential surface of the connecting part 98, a positioning projection 110 extending in the axial direction in the widthwise center is provided on the proximal end side with respect to the locking part 104.

The connecting member 94 having such a structure is fitted into the passage hole 92, and the protector 52 is inserted from the distal end side of the large diameter tube part 84, so that the protector 52 is inserted through the through hole 100 as well. With this configuration, the flat plate parts 58, 58 of the protector 52 are in contact not only with the inner surface of the large diameter tube part 84 but also with the inner surface of the through hole 100. This makes it possible to prevent the connecting member 94 from falling out of the passage hole 92.

The inner needle unit 16 and the outer needle unit 22 having the above structure are attached and connected to each other. That is, the inner needle 12 extending from the inner needle hub 14 through the protector 52 to the distal end side is inserted from the proximal end opening part 30 of the outer needle hub 20, and is inserted through the hemostasis valve mechanism 36 and the outer needle 18, so as to protrude to the distal end side with respect to the outer needle 18.

With this configuration, the locking part 104 projecting to the distal end side with respect to the first tubular body 60 is locked to the flanged part 32 of the outer needle hub 20 from the outside, while the distal end portion of the large diameter tube part 84 of the third tubular body 64 projecting to the distal end side with respect to the rectangular tube part 66 is inserted into the inside of the outer needle hub 20 from the proximal end opening part 30 of the outer needle hub 20. At the distal end portion of the large diameter tube part 84, the portion inserted in the inside of the outer needle hub 20 comprises the insertion part 112, and the peripheral wall 26 of the outer needle hub 20 is sandwiched by the locking part 104 and the insertion part 112 from the inside and the outside.

In particular, in the present practical embodiment, the positioning groove 34 of the flanged part 32 and the positioning projection 110 of the connecting part 98 are positioned in the circumferential direction, and the positioning projection 110 is inserted into the positioning groove 34. With this configuration, relative rotation of the inner needle unit 16 and the outer needle unit 22 is prevented.

The method of using the indwelling needle assembly 10 as described above will be described with reference to FIGS. 8 to 11. First, the indwelling needle assembly 10 is stuck into the blood vessel of the patient with the inner needle 12 and the outer needle 18 overlapped with each other. After confirming the flashback at the storing tube part 48 or the distal end portion of the outer needle hub 20, for example, the opposite side surfaces (the opposite side surfaces in the left-right direction in FIG. 2) of the rectangular tube part 66 of the inner needle hub 14 are grasped by the fingers, and the inner needle 12 is retracted from the outer needle 18 to the proximal end side. By so doing, the first tubular body 60 located on the most proximal end side of the inner needle hub 14 moves to the proximal end side.

Then, when the first tubular body 60 moves to the proximal end side to some extent, the first engaging claw 76 and the second proximal end engaging claw 80 engage with each other, and after their engagement, the second tubular body 62 moves to the proximal end side together with the first tubular body 60. Further, when the second tubular body 62 moves to the proximal end side to some extent, the second distal end engaging claw 82 and the third engaging claw 90 engage with each other. That is, by retracting the inner needle 12 toward the proximal end side, the first and second tubular bodies 60, 62 are configured to be sequentially pulled out toward the proximal end side. At this point, the locking part 104 of the connecting member 94 attached to the third tubular body 64 is locked to the flanged part 32 of the outer needle hub 20, so that the third tubular body 64 does not move to the proximal side. The first tubular body 60, the second tubular body 62, and the third tubular body 64 may be relatively rotatable, or may alternatively be relatively nonrotatable by being engaged with one another in the circumferential direction while being allowed to relatively move in the pull-out direction due to, for example, concave and convex parts or the like extending in the length direction.

Figure 9:
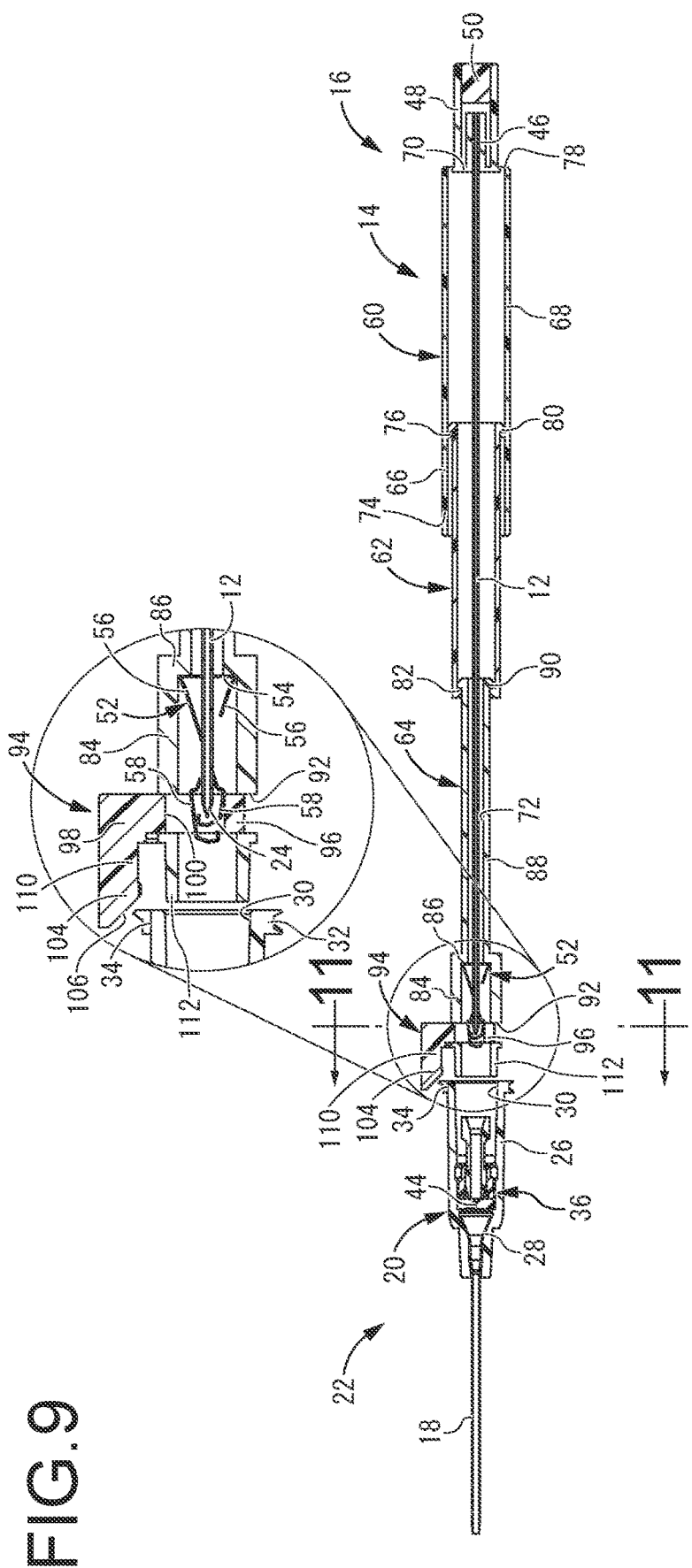
FIG. 9 is a vertical cross sectional view of the indwelling needle assembly of FIG. 8, corresponding to FIG. 4.
Figure 10:
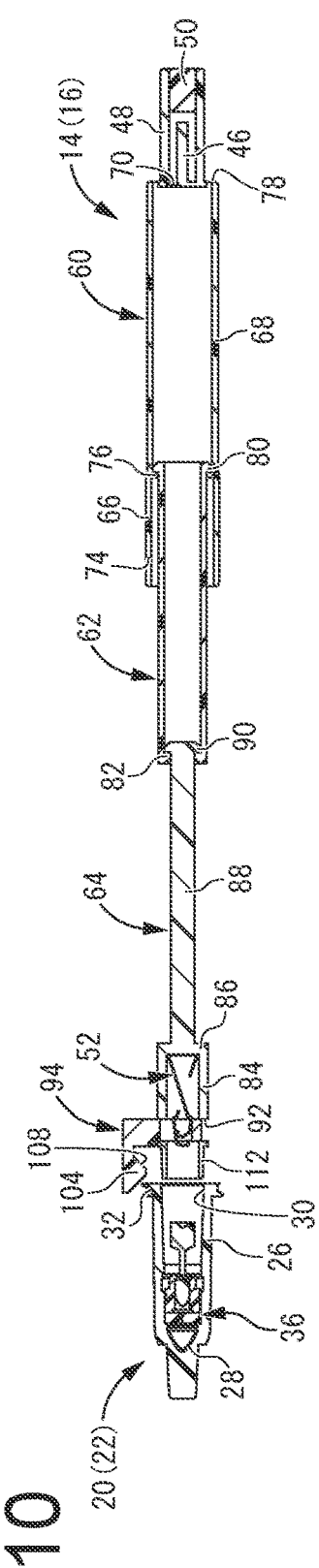
FIG. 10 is a vertical cross sectional view of the indwelling needle assembly of FIG. 8, corresponding to FIG. 5.

Here, as shown in FIG. 9, in a state where the first and second tubular bodies 60, 62 are pulled out to the most proximal end side and the inner needle 12 is moved to the most proximal end side, the needle tip 24 of the inner needle 12 is located inside the protector 52, and is located on the proximal end side with respect to the contact position with the distal end portions of the elastic arm parts 56, 56. That is, when the inner needle 12 is retracted toward the proximal end side, the contact between the inner needle 12 and the distal end portions of the elastic arm parts 56, 56 is released, and the distal end portions of the elastic arm parts 56, 56 follow the urging force to deform in the direction of approaching each other. By so doing, the distal end side of the inner needle 12 with respect to the needle tip 24 is covered with the distal end portions of the elastic arm parts 56, 56, and the needle tip 24 of the inner needle 12 is protected. Besides, even if an external force in the direction of moving to the distal end side is exerted on the inner needle 12, the needle tip 24 comes into contact with the distal end portions of the elastic arm parts 56, 56, thereby preventing re-exposure of the needle tip 24 of the inner needle 12. In the present practical embodiment, since the retracted inner needle 12 is covered with the first, second, and third tubular bodies 60, 62, 64 and the protector 52 across the entire length, a full-cover type protector is provided.

In short, the present practical embodiment provides a full-cover type protector, and the retracted inner needle 12 including the needle tip 24 is covered with the first, second, and third tubular bodies 60, 62, 64 across the entire length. Further, the protector 52 is positioned in the axial direction with respect to the third tubular body 64. Thus, in the state where the inner needle 12 is retracted and the needle tip 24 is covered with the protector 52, even if an external force is applied in the direction of contracting the first, second, and third tubular bodies 60, 62, 64 by any chance, the needle tip 24 of the inner needle 12 hits the protector 52, so that the first, second, and third cylinders are prevented from being contracted, thereby preventing re-exposure of the inner needle 12.

Further, in the present practical embodiment, as described above, by simply operating the first tubular body 60 fixed to the proximal end of the inner needle 12 in the pull-out direction, the second and third tubular bodies 62, 64 are configured to be stretched in conjunction therewith so as to cover the inner needle 12 retracted from the outer needle unit 22 at the same time of being pulled out. Moreover, the protector 52 attached to the third tubular body 64 is configured to cover the needle tip 24 of the inner needle 12 at the same time of being pulled out. Therefore, it is not necessary to lock the first to third tubular bodies 60, 62, 64 and the protector 52 by the inner needle 12 and interlock them in the pull-out direction, and there is no need to provide a partial protrusion, a large-diameter part, or the like on the outer circumferential surface of the inner needle 12. For this reason, in addition to preventing a situation in which such a large-diameter part or the like interferes with the protector 52 and causes an accidental movement of the protector 52 when the inner needle 12 is retracted, the number of interlocking members acting in the pull-out direction can be reduced, thereby improving the operational stability as well.

Then, the elastic arm parts 56, 56 elastically deform in the direction of approaching each other, so that the contact between the flat plate parts 58, 58 and the inner surfaces of the large diameter tube part 84 and the through hole 100 is released. Accordingly, the connecting member 94 fitted and positioned in the passage hole 92 becomes displaceable in the direction of detachment from the passage hole 92.

Here, by further retracting the inner needle 12, the proximal side end face 108 of the locking part 104 locked to the flanged part 32 comes into contact with the flanged part 32. By so doing, since the connecting member 94 displaceable in the direction of detachment from the passage hole 92, by retracting the inner needle 12, the connecting member 94 moves along the proximal side end face of the locking part 104, which is the inclined surface, to the outer side (the lateral side of the indwelling needle assembly 10, namely the left side in FIG. 2), so that the lock of the locking part 104 to the flanged part 32 is released.

Then, by further retracting the inner needle 12 toward the proximal end side, the insertion part 112 inserted in the outer needle hub 20 in the third tubular body 64 is also retracted from the outer needle hub 20, so that inner needle unit 16 can be detached from the outer needle unit 22. Subsequently, for example, the outer needle hub 20 is pushed into the blood vessel side of the patient (delivery operation), and the distal end of the outer needle 18 is sufficiently inserted into the blood vessel of the patient so that the outer needle unit 22 is indwelled. By connecting a syringe or the like to the outer needle hub 20, it becomes possible to inject a drug solution or the like in the syringe into the patient.

Figure 11:
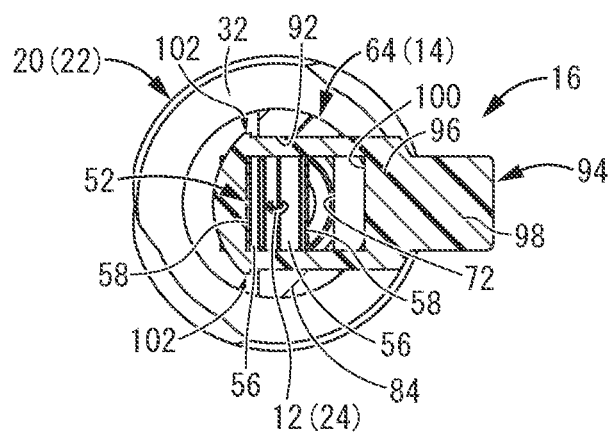
FIG. 11 is an enlarged transverse cross sectional view taken along line 11-11 of FIG. 9.

In particular, in the present practical embodiment, at the end of the passage part 96 of the connecting member 94 on the side opposite to the direction of displacement of the connecting member 94, the retaining projections 102, 102 projecting to the outer side in the width direction with respect to the opening peripheral edge of the passage hole 92 are provided. With this configuration, as shown in FIG. 11, by the retaining projections 102, 102 coming into contact with the opening peripheral edge of the passage hole 92, the connecting member 94, which is displaceable with respect to the passage hole 92, can be prevented from falling out of the passage hole 92. Indeed, by the protector 52 being inserted through the through hole 100 of the passage part 96 as well, the connecting member 94 can be prevented from falling out of the passage hole 92.

In the indwelling needle assembly 10 of the present practical embodiment having the above structure, due to the retraction of the inner needle 12, the locking part 104 and the flanged part 32 of the outer needle hub 20 are unlocked, so that inner needle unit 16 can be detached from the outer needle unit 22. In particular, the connecting member 94 moves along the proximal side end face 108 of the locking part 104, which is the inclined surface. Accordingly, it is possible to avoid a cumbersome operation required of the indwelling needle assembly of the conventional structure in which, after retraction of the inner needle, the inner needle unit and the outer needle unit are moved in the directions opposite to each other.

Besides, in the initial state before the inner needle 12 is retracted, the peripheral wall 26 of the outer needle hub 20 is sandwiched by the locking part 104 and the insertion part 112 at the distal end of the third tubular body 64 from the inside and the outside. Thus, the connected state of the inner needle unit 16 and the outer needle unit 22 can be stably maintained.

Moreover, in the initial state before the inner needle 12 is retracted, the flat plate parts 58, 58 of the protector 52 are in planar contact with both the inner surface of the large diameter tube part 84 and the inner surface of the through hole 100. Therefore, the connecting member 94 can be more reliably prevented from falling out of the passage hole 92, and the position shift of the protector 52 within the third tubular body 64 can also be effectively prevented.

Furthermore, the connecting member 94 displaces so as to project laterally from the indwelling needle assembly 10. Thus, even if the user places his or her finger on the side of top surface (the upper surface in FIG. 2) of the outer needle hub 20, the movement of the connecting member 94 is less likely to be interfered, and it is easy for the user to push out the outer needle hub 20 toward the distal end side with a finger. That is, the connecting member 94 does not interfere with the delivery operation of the outer needle hub 20 or is not pressed against the skin of the patient, and the displacement of the connecting member 94 is stably realized. Hence the disconnection of the inner needle unit 16 and the outer needle unit 22 can also be achieved more reliably.

Further, in the present practical embodiment, the inner needle hub 14 has a multi-cylinder structure, and by sequentially pulling out the plurality of tubular bodies (the first and second tubular bodies 60, 62 in the practical embodiment), the inner needle 12 will be stored in the inner needle hub 14. By adopting such a structure, the axial length of the inner needle hub 14 can be reduced, and the indwelling needle assembly 10 can be downsized. In particular, the first, second, and third tubular bodies 60, 62, 64 are disposed within one another on the proximal end side with respect to the attachment position of the protector 52 in the third tubular body 64 (the large diameter tube part 84). Therefore, in comparison with the case where, for example, a plurality of tubular bodies are disposed within one another on the radially outer side of the attachment position of the protector, it is possible to avoid increase in diameter of the inner needle hub 14.

Moreover, the penetration hole 78 is formed so as to penetrate through the proximal end wall 70 of the first tubular body 60 located on the most proximal end side of the inner needle hub 14. Thus, when the first and second tubular bodies 60, 62 are pulled out, a large negative pressure will not be formed inside the inner needle hub 14, and the first and second tubular bodies 60, 62 can be pulled out smoothly. In particular, even in the case of a telescopic structure in which a plurality of tubular bodies are disposed within one another in multiple layers, the external air can be quickly introduced into the inner tubular body because the proximal end wall 70 communicates with the outside.

Figure 12:
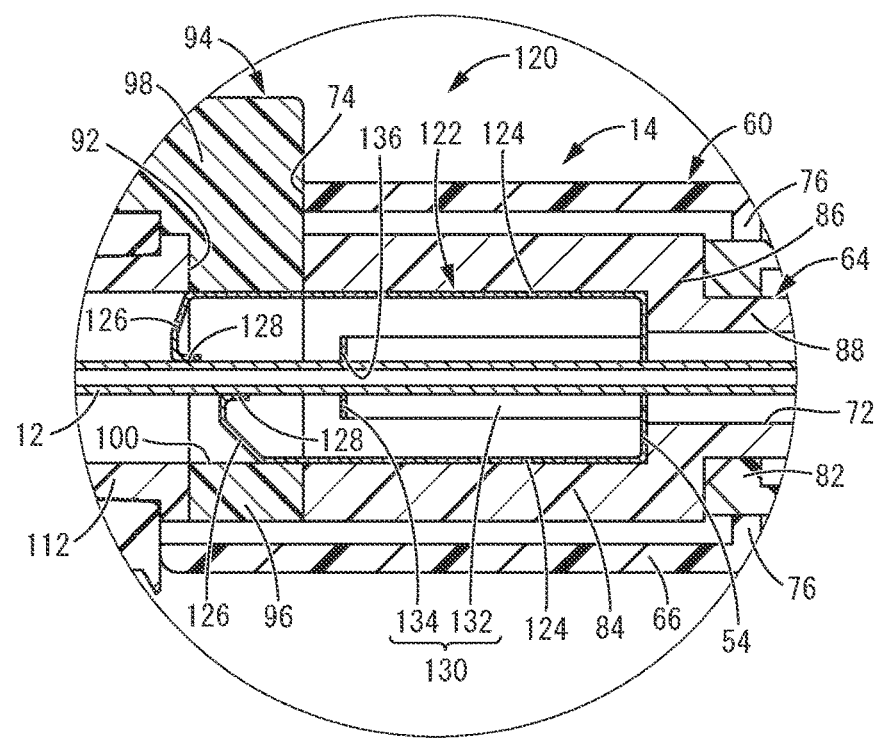
FIG. 12 is a cross sectional view showing a part of an indwelling needle assembly according to a second practical embodiment of the present invention.

FIG. 12 shows a part of an indwelling needle assembly 120 according to a second practical embodiment of the present invention. The indwelling needle assembly 120 has a structure in which a protector 122 serving as a preventing member and serving as a displacing member is stored in the large diameter tube part 84 of the inner needle hub 14 constituting the storage housing.

Like the protector 52 of the first practical embodiment, the protector 122 is made of, for example, a pressed product of spring steel, and is allowed to elastically deform. The protector 122 includes the rear wall 54 and a pair of elastic arm parts 124, 124 projecting from the opposite end parts (opposite end parts in the vertical direction in FIG. 12) of the rear wall 54 toward the distal end side. The elastic arm parts 124, 124 each have a generally flat-plate shape, and their distal end portions are movable relative to each other in the direction of approaching or in the direction of separating from each other due to bending elastic deformation in the plate thickness direction. The elastic arm parts 124, 124 extend without intersecting with each other, and their distal ends are separated from each other. The elastic arm parts 124, 124 have different axial dimensions from each other, as in the elastic arm parts 56, 56 of the first practical embodiment.

A convex part (not shown) is formed on the outer surface of the rear wall 54, while a concave part (not shown) is formed on the inner surface of the large diameter tube part 84, and the concave part of the large diameter tube part 84 engages with the convex part of the rear wall 54. Therefore, the protector 122 is locked to the large diameter tube part 84 regardless of before or after the displacement of the elastic arm parts 124, 124, and the protector 122 is prevented from slipping out to the opening side (the left side in the drawing) of the large diameter tube part 84. Further, the inner circumferential shape of the large diameter tube part 84 and the outer circumferential shape of the rear wall 54 in the cross section orthogonal to the inner needle 12 are generally corresponding rectangular shapes, and the protector 122 is formed so as to be in a predetermined rotating position around the axis with respect to the large diameter tube part 84. The inner needle 12 may be provided with a convex part that cannot pass through the hole of the rear wall 54 to restrict the movement of the protector 122 with respect to the inner needle 12. Further, the inner surface of the large diameter tube part 84 and the outer surface of the protector 122 may be provided with engaging portions due to concave and convex parts or the like so that the protector 122 does not rotate about the axis with respect to the large diameter tube part 84. The rotation of the protector 122 with respect to the large diameter tube part 84 may be restricted by forming a guide convex and a guide concave extending in the axial direction.

At the distal end of each elastic arm part 124, there is provided a needle-tip protection part 126 that spreads while inclining with respect to the elastic arm part 124. The needle-tip protection part 126 projects inward in the direction of opposition (the vertical direction in FIG. 12) of the elastic arm parts 124, 124. The end of the needle-tip protection part 126 comprises a sliding contact part 128 bent so as to face generally parallel to the elastic arm part 124, so as to be prevented from getting caught or the like when the needle-tip protection part 126 comes into contact with the outer circumferential surface of the inner needle 12.

The inner needle 12 is inserted between the pair of needle-tip protection parts 126, 126, and the needle-tip protection parts 126, 126 are pushed apart by the inner needle 12 in a direction in which they are separated from each other, so that the elastic arm parts 124, 124 are in the elastically deformed state shown in FIG. 12. The elastic arm parts 124, 124 in the elastically deformed state are pressed against the inner circumferential surfaces of the large diameter tube part 84 of the inner needle hub 14 and the connecting member 94, so that the connecting member 94 and the large diameter tube part 84 are positioned relative to each other in the axis-perpendicular direction. In the present practical embodiment, generally the entire elastic arm parts 124, 124 are in contact with the inner circumferential surfaces of the large diameter tube part 84 and the connecting member 94. However, for example, only the distal end portion of the elastic arm part 124 may be in contact with the inner circumferential surfaces of the large diameter tube part 84 and the connecting member 94.

The protector 122 includes a guide part 130. The guide part 130 projects toward the distal end side from the portion away from the elastic arm parts 124, 124 in the outer peripheral end of the rear wall 54. The guide part 130 includes a support part 132 extending in the axial direction and a needle passage part 134 protruding at the distal end of the support part 132 in the direction in which the inner needle 12 is located. The needle passage part 134 has, for example, a plate shape extending in the axis-perpendicular direction, and has a guide hole 136 penetrating in the axial direction. The guide hole 136 is located on the needle axis of the inner needle 12 inserted through the protector 122 in a state where the protector 122 is attached to the inner needle hub 14, and the inner needle 12 can be inserted through the guide hole 136. The guide hole 136 may be a notch hole in which a part of the periphery is opened, or the like, other than the penetration hole shown in the present practical embodiment. When a notch hole is adopted as the guide hole 136, it is desirable that the guide hole 136 is opened in the direction of opposition of the pair of elastic arm parts 124, 124 in order to position the inner needle 12 in the direction orthogonal to the direction of opposition of the elastic arm parts 124, 124. Besides, two guide parts 130 each having a notch hole may be provided so as to be opposed to each other, so that the inner needle 12 is inserted through the notch holes of the guide parts 130.

Figure 13:
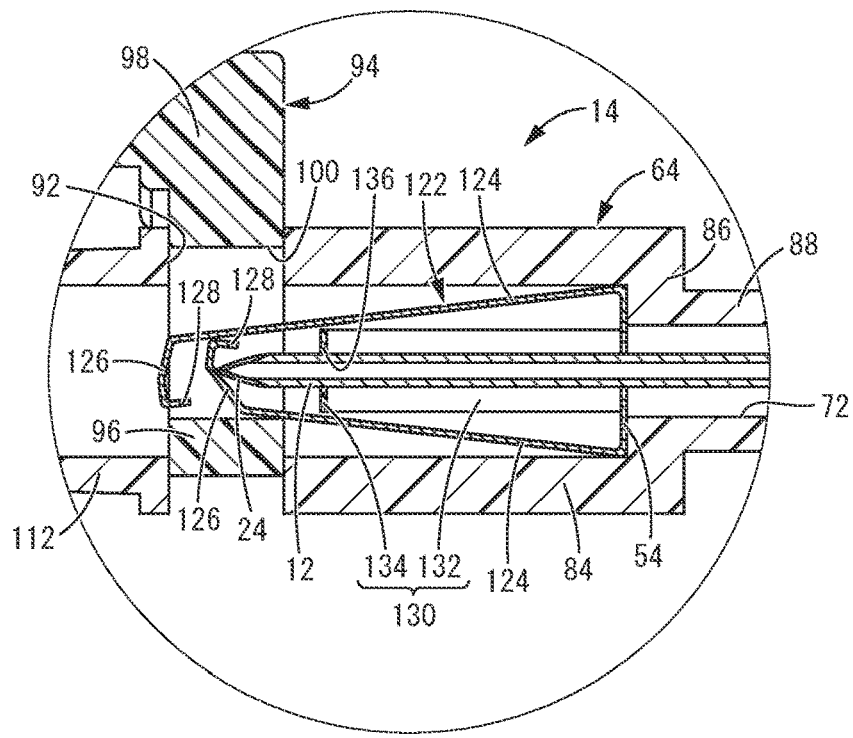
FIG. 13 is a cross sectional view of the indwelling needle assembly of FIG. 12, showing a part of an inner needle unit after an inner needle is retracted from an outer needle unit.

In the indwelling needle assembly 120 provided with the protector 122 as described above, when the inner needle 12 is retracted from the outer needle unit (not shown) after puncture, and the inner needle 12 moves to more proximal end than the location between the needle-tip protection parts 126, 126 of the protector 122, the elastic arm parts 124, 124 that have been pushed apart by the inner needle 12 recover to their original shapes. That is, as shown in FIG. 13, the elastic arm parts 124, 124 incline so that the distal end sides approach each other, and the needle-tip protection parts 126, 126 provided at the distal ends of the elastic arm parts 124, 124 approach each other and move to the distal end side on the extension of the needle axis of the inner needle 12. By so doing, the distal end side of the inner needle 12 with respect to the needle tip 24 is covered by the needle-tip protection parts 126, 126, and re-projection of the inner needle 12 is prevented by the protector 122, thereby preventing inadvertent puncture of the inner needle 12 or the like.

The protector 122 includes the guide part 130, and the inner needle 12 is inserted through the guide hole 136 of the guide part 130. With this configuration, the relative tilt of the inner needle 12 with respect to the protector 122 is restricted, and in particular, the needle tip 24 is prevented from moving to the lateral side (in the direction orthogonal to the paper surface in FIG. 13) with respect to the protector 122. Therefore, it is possible to prevent the needle tip 24 from being exposed laterally from the protector 122, and the needle tip 24 is effectively protected by the protector 122. Since the guide part 130 is arranged at a position away from the rear wall 54 through which the inner needle 12 penetrates, the inner needle 12 is positioned with the protector 122 at two places separated in the needle axis direction by the guide part 130 and the rear wall 54, thereby more effectively preventing the tilt of the inner needle 12 with respect to the protector 122.

However, in the present practical embodiment, the needle passage part 134 need not be provided, and the guide part 130 itself is not essential. When the needle passage part 134 is not provided, the support part 132 is located on the lateral side of the inner needle 12, so that the tilt of the inner needle 12 to the lateral side is restricted. Further, it would also be acceptable to provide a plate-shaped part extending inward from the side part of the elastic arm parts 124, 124, so that when the inner needle 12 is retracted or after the protector 122 operates, the inner needle 12 is configured to be surrounded by the elastic arm part 124, 124 and the said plate-shaped part, and the inner needle 12 is easily held at the opposed position of the elastic arm parts 124, 124. In the case of providing such a plate-shaped part or the like, the holding of the inner needle 12 can be realized without providing the guide part 130. Further, it would also be possible to provide a groove or a notch in the contact portion with the inner needle 12 in the sliding contact part 128 of the elastic arm parts 124, 124, so that the inner needle 12 is less likely to deviate from the sliding contact part 128.

In the preceding first practical embodiment, the protector 52 having a structure in which the elastic arm parts 56, 56 extend so as to intersect with each other is illustrated, but the protector 122 having a structure in which the elastic arm parts 124, 124 do not intersect with each other as shown in the present practical embodiment can also be adopted. The indwelling needle assembly 120 according to the present practical embodiment also exhibits the same effect as the indwelling needle assembly 10 according to the preceding first practical embodiment.

Although the practical embodiments of the present invention have been described above, the present invention is not limitedly interpreted based on the specific description in the practical embodiment, but may be embodied with various changes, modifications and improvements which may occur to those skilled in the art.

For example, in the preceding practical embodiments, the storage housing in which the protector 52 is stored is constituted by the inner needle hub 14, but the present invention is not limited to such embodiments. That is, it would also be acceptable that the fixing tube part (and the storing tube part) that supports the inner needle has a structure separate from the first tubular body, and the inner needle extends to the distal end side through a center hole provided in the center of the proximal end wall of the first tubular body. Besides, a large-diameter part is provided on the inner needle, and by the large-diameter part of the inner needle and the opening peripheral edge of the center hole coming into contact with each other when the inner needle is retracted, the first tubular body is pulled out at the same time of the retraction of the inner needle. By so doing, the inner needle is protected by the first, second, and third tubular bodies and the protector as in the preceding practical embodiments. That is, the storage housing need not have a function as the inner needle hub.

Further, in the preceding practical embodiments, the insertion part 112 that sandwiches the peripheral wall 26 of the outer needle hub 20 in cooperation with the locking part 104 is constituted by the distal end portion of the large diameter tube part 84, but the insertion part may be constituted by a half-split tubular body or a projecting piece partially provided in the circumferential direction. However, the insertion part is not essential. For example, on the peripheral wall end face where the proximal end surface of the outer needle hub 20 and the distal end surface of the large diameter tube part 84 of the third tubular body 64 are abutted, a hole and a protrusion inserted into the hole in the axial direction may be formed, or an insertion part into the outer needle hub 20 may be provided at the distal end portion of the first tubular body 60. Alternatively, the protector 52 may be projected into the outer needle hub 20 to be inserted.

Moreover, the structure of the protector is not limited. For example, the elastic arm parts need not intersect each other and may extend within the outer needle hub. However, the protector is not essential. For example, by providing a locking mechanism to the plurality of pulled-out tubular bodies for preventing movement in the direction opposite to the pull-out direction, the re-exposure of the needle tip of the inner needle can be prevented. It is not essential that the needle tip of the inner needle is protected. Further, the protector 52 of the preceding practical embodiment has a function of preventing the movement of the plurality of tubular bodies in the direction of contraction, a protector function of covering the needle tip 24, and a function of releasing the movement prevention of the connecting member 94 due to retraction of the inner needle 12. However, by adopting a locking mechanism that prevents movement in the direction of contraction in the plurality of pulled-out tubular bodies, or by providing a member that blocks the distal end of the tubular body is separately provided on the proximal end side with respect to the protector 52, it is possible to have only the function of releasing the movement prevention of the connecting member 94 due to retraction of the inner needle 12 (there is no protector function).

Furthermore, in the preceding practical embodiments, the inner needle hub 14 is constituted by the plurality of tubular bodies (first, second, and third tubular bodies 60, 62, 64) being disposed within one another. However, for example, the inner needle hub 14 may be constituted by a single tubular body having a length generally equal to the entire length of the inner needle, such as a tubular body having a bellows structure. Besides, the tubular body is not limited to a full-cover type as in the practical embodiment, but it would also be possible to adopt a partial-cover type tubular body that covers only a part of the inner needle, and the protector may be stored in the said tubular body and the connecting member may be attached thereto.

Additionally, in the preceding practical embodiments, when the inner needle 12 is inserted through the protector 52, the elastic arm parts 56, 56 and the inner needle 12 are in direct contact with each other. However, it would also be acceptable that a sleeve is externally placed about the inner needle, and by the said sleeve and the elastic arm parts coming into contact with each other, the elastic deformation of the elastic arm parts is prevented. In this case, for example, it would also be possible that the inner needle is provided with a large-diameter part that engages with the sleeve, and the sleeve moves to the proximal end side due to the retraction of the inner needle so that the contact with the elastic arm parts is released. With this configuration, the sliding resistance during the retraction of the inner needle can be reduced. However, the present invention is not limited to such a sleeve. The present invention may adopt an interlocking member that interlocks with the retraction of the inner needle, and may adopt a mechanism that allows the preventing member to move or deform by the said interlocking member. Further, the member that interlocks with the retraction of the inner needle and the member that allows the preventing member to move or deform due to displacement may be separate members from each other, and the latter may be displaced by the former. When a sleeve or the like is provided, since the number of interlocking members in the pull-out direction increases, there may be disadvantages such as difficulty in realizing stable performance, complicated configuration, and increase in size of the protection housing, and as a result, the operability of the practitioner may be reduced.

Besides, in the preceding practical embodiments, the protector 52 that protects the needle tip by elastic deformation due to the retraction of the inner needle 12 is adopted, but as described in International Publication No. WO 2013/027355, for example, it is also possible to employ a protector or the like that is allowed to displace due to the retraction of the inner needle by utilizing a magnetic force.

Further, in the preceding practical embodiments, the preventing member provided between the inner needle 12 and the connecting member 94 to prevent the movement of the connecting member 94 thereby holding the storage housing 14 and the outer needle hub 20 in the connected state is constituted by the protector 52 that protects the needle tip 24 of the inner needle 12. However, it is also possible to constitute such a preventing member by a separate member from the protector that protects the needle tip. Specifically, for example, in the preceding practical embodiments, by arranging a needle tip protector as described in the above-mentioned WO2013/027355 or the like that protects the needle tip by being displaced by a magnetic force due to the retraction of the inner needle on the proximal end side of the large diameter tube part 84 of the third tubular body 64 constituting the storage housing, it is also possible to provide the preventing member that exhibits functions to hold and release the connected state by the connecting member 94 separately from the said needle tip protector without having the function of protecting the needle tip due to the retraction of the inner needle.

Additionally, the preventing member is not limited to the illustrated one that releases the connected state by the connecting member 94 by elastic deformation due to the retraction of the inner needle. For example, similar to the above-mentioned needle tip protector, a preventing member that, due to the retraction of the inner needle, releases the connected state by the connecting member by being displaced by a magnetic force can be adopted. It would alternatively be possible to adopt a preventing member that, due to the retraction of the inner needle, releases the connected state by the connecting member by being displaced by utilizing a spring separately provided, or a preventing member that, due to the retraction of the inner needle, releases the connected state by the connecting member by being displaced by utilizing gravity by its own weight, and the like.

Further, in the preceding practical embodiments, the connecting member 94 that is directly locked to the outer needle hub 20 is adopted, but it is acceptable as long as the connecting member can connect the storage housing provided on the inner needle unit side to the outer needle unit. For example, when a separate detachable member is attached to the outer needle hub, as long as the said separate member will not be detached from the outer needle hub until the inner needle hub is retracted, it is conceivable that the outer needle unit is constituted by including the said separate member, or is conceivable to be connected to the outer needle hub via the said separate member. For example, it would be acceptable to connect a member for covering the proximal end of the outer needle hub to prevent exposure or a hemostatic member to the outer needle hub before the connection with the inner needle hub so as to form the outer needle hub unit. For example, the outer needle hub may be constituted by fixing a plurality of tubular members. Therefore, the connecting member in the present invention may be locked to a separate member from such an outer needle hub. Besides, in the preceding practical embodiments, the connecting member is a member that engages with the outer surface of the outer needle hub, but may be a member that engages with the inner surface of the outer needle hub. For example, it would also be acceptable to form notches that open at the distal end of the insertion part 112 and extend in the axial direction at two locations in the circumferential direction, and to form an arm serving as a connecting member circumferentially between the notches, the arm being movable in the axis-perpendicular direction of the inner needle 12 by flexural deformation, and by locating the protector 122 inside the arm, the connection with the outer needle hub 20 may be realized. Further, for example, it would also be possible to form an annular concave part or a convex part on the inner surface of the pusher 40 or the like and to engage the protector 122 with the inner surface of the pusher 40, so that the protector 122 itself has a function of connection with the outer needle hub 20. In any of these cases, the arm or the protector constituting the connecting member is allowed to move by the deformation or displacement of the protector due to the retraction of the inner needle, thereby releasing the connected state of the storage housing to the outer needle hub.

KEYS TO SYMBOLS

10, 120: indwelling needle assembly, 12: inner needle, 14: inner needle hub (storage housing, protection housing), 16: inner needle unit, 18: outer needle, 20: outer needle hub, 22: outer needle unit, 24: needle tip, 26: peripheral wall, 28: caulking pin, 30: proximal end opening part, 32: flanged part, 34: positioning groove, 36: hemostasis valve mechanism, 38: disc valve, 40: pusher, 42: pusher guide, 44: slit, 46: fixing tube part, 48: storing tube part, 50: ventilation filter, 52, 122: protector (preventing member), 54: rear wall, 56, 124: elastic arm part, 58: flat plate part, 60: first tubular body, 62: second tubular body, 64: third tubular body, 66: rectangular tube part, 68: cylinder part, 70: proximal end wall, 72: inner hole, 74: notch, 76: first engaging claw, 78: penetration hole, 80: second proximal end engaging claw, 82: second distal end engaging claw, 84: large diameter tube part, 86: annular wall, 88: small diameter tube part, 90: third engaging claw, 92: passage hole, 94: connecting member, 96: passage part, 98: connecting part, 100: through hole, 102: retaining projection, 104: locking part, 106: distal side end face, 108: proximal side end face, 110: positioning projection, 112: insertion part, 126: needle-tip protection part, 128: sliding contact part, 130: guide part, 132: support part, 134: needle passage part, 136: guide hole

The invention claimed is:

1. An indwelling needle assembly comprising:
an inner needle unit including an inner needle hub;
an outer needle unit including an outer needle hub, the inner needle unit and the outer needle unit being detachably connected to each other;
an inner needle to which a protector is attached, the inner needle being retractably inserted through an outer needle, while the protector being configured to deform or displace to protect a needle tip of the inner needle by being moved to the needle tip due to retraction of the inner needle;
a storage housing storing the protector, the storage housing being provided to the inner needle unit; and
a connecting member connecting the storage housing to the outer needle hub, wherein
the protector prevents the connecting member from moving such that the storage housing and the outer needle hub are held in a connected state, and
the connecting member is configured to be permitted to move by the protector deforming or displacing due to the retraction of the inner needle such that the connected state of the storage housing and the outer needle hub is allowed to be released, wherein
the connecting member includes a locking part locked to a proximal end opening part of the outer needle hub,
a distal end portion of the storage housing is inserted from the proximal end opening part of the outer needle hub, and
a peripheral wall of the outer needle hub is sandwiched by the locking part of the connecting member and the distal end portion of the storage housing from an inside and an outside.

2. An indwelling needle assembly comprising:
an inner needle unit including an inner needle hub;
an outer needle unit including an outer needle hub, the inner needle unit and the outer needle unit being detachably connected to each other;

an inner needle to which a protector is attached, the inner needle being retractably inserted through an outer needle, while the protector being configured to deform or displace to protect a needle tip of the inner needle by being moved to the needle tip due to retraction of the inner needle;

a storage housing storing the protector, the storage housing being provided to the inner needle unit; and a connecting member connecting the storage housing to the outer needle hub, wherein the protector prevents the connecting member from moving such that the storage housing and the outer needle hub are held in a connected state, the connecting member is configured to be permitted to move by the protector deforming or displacing due to the retraction of the inner needle such that the connected state of the storage housing and the outer needle hub is allowed to be released, and the connecting member includes a through hole communicating with an inner hole of the storage housing, and the protector, the protector being prevented from elastic deformation by the inner needle being inserted through the protector, is in contact with both inner surfaces of the inner hole and the through hole such that the connecting member is prevented from moving with respect to the storage housing.

3. The indwelling needle assembly according to claim 1, wherein contact portions between an inner surface of the storage housing and the protector, the protector being prevented from elastic deformation by the inner needle being inserted through the protector, are in planar contact with each other.

4. The indwelling needle assembly according to claim 1, wherein the storage housing includes a pair of grasping parts provided on an outer circumferential surface of the storage housing in a portion located on a distal end side.

5. The indwelling needle assembly according to claim 1, wherein an inclined surface is provided in a portion where the connecting member and the outer needle hub are locked, and the connecting member is configured to move along the inclined surface due to the retraction of the inner needle such that connection between the connecting member and the outer needle hub is released.

* * * * *